United States Patent
Bottom (10) Patent No.: US 10,668,243 B2
(45) Date of Patent: Jun. 2, 2020

(54) ANESTHESIA COMPLIANT VOLUME SYSTEM AND METHOD

(71) Applicant: General Electric Company, Schenectady, NY (US)

(72) Inventor: Douglas Kirk Bottom, Watertown, WI (US)

(73) Assignee: General Electric Company, Schenectady, NY (US)

( * ) Notice: Subject to any disclaimer, the term of this patent is extended or adjusted under 35 U.S.C. 154(b) by 1661 days.

(21) Appl. No.: 14/327,159

(22) Filed: Jul. 9, 2014

(65) Prior Publication Data

US 2016/0008567 A1    Jan. 14, 2016

(51) Int. Cl.
| | |
|---|---|
| *A61M 16/18* | (2006.01) |
| *A61M 16/10* | (2006.01) |
| *A61M 16/01* | (2006.01) |
| *A61M 16/00* | (2006.01) |

(Continued)

(52) U.S. Cl.
CPC .......... *A61M 16/18* (2013.01); *A61M 11/045* (2014.02); *A61M 16/0057* (2013.01); *A61M 16/0075* (2013.01); *A61M 16/01* (2013.01); *A61M 16/104* (2013.01); *A61M 16/1075* (2013.01); *A61M 16/20* (2013.01); *A61M 16/203* (2014.02); *A61M 2016/003* (2013.01); *A61M 2016/1035* (2013.01); *A61M 2202/0208* (2013.01); *A61M 2202/0283* (2013.01); *A61M 2205/3334* (2013.01);

(Continued)

(58) Field of Classification Search
CPC .. A61M 16/18; A61M 11/045; A61M 16/203; A61M 16/0057; A61M 16/0075; A61M 16/01; A61M 16/104; A61M 16/1075; A61M 16/20; A61M 2016/003; A61M 2016/1035; A61M 2202/0208; A61M 2202/0283; A61M 2205/3334; A61M 2205/3653; A61M 2205/3673; F16L 55/02; F16L 55/04; F16L 55/041; F16L 55/043
USPC .................................................... 128/200.23
See application file for complete search history.

(56) References Cited

U.S. PATENT DOCUMENTS

| | | |
|---|---|---|
| 5,390,665 A | 2/1995 | Leach |
| 5,509,405 A | 4/1996 | Mashak |
| 5,636,626 A | 6/1997 | Bloch et al. |

(Continued)

FOREIGN PATENT DOCUMENTS

| | | | |
|---|---|---|---|
| EP | 0911053 A2 * | 4/1999 | ............ A61M 16/18 |
| GB | 2400566 A * | 10/2004 | ............ A61M 16/18 |
| WO | 9219303 A1 | 11/1992 | |

OTHER PUBLICATIONS

PulseGuard, Pulsation Dampeners for Flow & Pressure, Jul. 7, 2013, http://pulseguard.com/ (Year: 2013).*

(Continued)

*Primary Examiner* — Kendra D Carter
*Assistant Examiner* — Elliot S Ruddie (57) ABSTRACT

A system for pressurizing liquid is described herein. The system may include a liquid reservoir and a pump coupled to the liquid reservoir, the pump to draw liquid from the liquid reservoir. A compliant volume coupled to the pump receives liquid from pump. The compliant volume is composed of an elastic material to increase pressure of the liquid. A valve coupled to the compliant volume receives pressurized liquid from the compliant volume.

15 Claims, 4 Drawing Sheets

(51) Int. Cl.
   *A61M 16/20* (2006.01)
   *A61M 11/04* (2006.01)
(52) U.S. Cl.
   CPC .............. *A61M 2205/3653* (2013.01); *A61M 2205/3673* (2013.01); *A61M 2205/505* (2013.01)

(56) References Cited

U.S. PATENT DOCUMENTS

| | | | |
|---|---|---|---|
| 5,645,052 A | 7/1997 | Kersey | |
| 6,443,150 B1* | 9/2002 | Pessala | A61M 16/18 128/203.12 |
| 2012/0318263 A1* | 12/2012 | Jones | A61M 16/01 128/203.12 |

OTHER PUBLICATIONS

International Search Report and Written Opinion for PCT/US2015/038501, dated Oct. 20, 2015, 9 pages.

* cited by examiner

ANESTHESIA COMPLIANT VOLUME SYSTEM AND METHOD

BACKGROUND

Anesthesia may be administered to a patient in the form of a gas to produce an effect such as pain management, unconsciousness, preventing memory formation, and/or paralysis. A predetermined dosage of the administered anesthetic may be inhaled into the patient's lungs to produce one or more of these effects.

Anesthesia systems may include an anesthesia machine coupled with a vaporizer system. Conventional vaporizer systems regulate anesthetic dosage in the gas phase. More precisely, some conventional vaporizer systems raise the temperature of the anesthetic to its vaporization point and thereafter regulate the concentration of delivered anesthetic gas such that the output concentration is maintained at a preselected target concentration.

One problem with some vaporizer systems is that a valve coupled to a vaporizer may be required to deliver varying flow rates of anesthetic liquid to the vaporizer. In some cases, valves having a larger range of liquid flow capability may be relatively expensive when compared to valves having a smaller range of liquid flow.

BRIEF DESCRIPTION

An embodiment relates to a system for pressurizing and depressurizing liquid. The system includes a liquid reservoir, and a pump coupled to the liquid reservoir. The pump is configured to draw liquid from and return liquid to the liquid reservoir. A compliant volume coupled to the pump is configured to receive liquid from and return liquid to the pump. The compliant volume is composed of an elastic material to increase the pressure of the liquid as its volume is increased. The system includes a valve coupled to the compliant volume. The valve is configured to receive pressurized liquid from the compliant volume.

Another embodiment relates to a method for pressurizing liquid. The method includes drawing liquid by a pump from a liquid reservoir. The method also includes receiving liquid from a pump at a compliant volume coupled to the pump. Pressure of the liquid is increased based on the elastance of the compliant volume. The method includes receiving pressurized liquid from the compliant volume at a valve coupled to the compliant volume.

Still another embodiment relates to an anesthetic vaporizer apparatus. The anesthetic vaporizer apparatus includes a liquid reservoir, and a pump coupled to the liquid reservoir. The pump is configured to draw liquid from the liquid reservoir. The anesthetic vaporizer apparatus includes a compliant volume coupled to the pump to receive liquid from the pump. The compliant volume is composed of an elastic material to increase the pressure of the liquid. The anesthetic vaporizer apparatus includes a valve coupled to the compliant volume to receive pressurized liquid from the compliant volume. The anesthetic vaporizer apparatus includes a vaporizer coupled to the valve to receive the pressurized liquid from the valve.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As discussed above, a valve coupled to a vaporizer may be required to deliver varying flow rates of anesthetic liquid to the vaporizer. In the embodiments discussed herein, a pump is coupled to a compliant volume. The compliant volume may be composed of a resilient and/or elastic material. As liquid is forced into the compliant volume, pressure of the liquid is increased as a result of the increasing counter force of the compliant volume to expansion. As liquid is removed from the compliant volume, pressure of the liquid is decreased as a result of the decreasing counter force of the compliant volume due to contraction. The pressurized liquid is then provided to a valve coupled to the compliant volume, and then to a vaporizer.

A resilient material, as referred to herein, is a material that is able to recoil or spring back into shape after bending, stretching, or being compressed. An elastic material, as referred to herein, is a material that produces an increasing counterforce with increasing volume, and a decreasing counterforce with decreasing volume.

A technical effect of at least one embodiment includes an expanded flow range. For example, rather than requiring a valve having a larger liquid flow range at a fixed input pressure, the valve may have a flow range that is relatively smaller due to the increase of liquid flow range of the valve when coupled to the compliant volume. In some scenarios, the liquid flow range of the valve may be effectively increased by association with the compliant volume from which the valve receives pressurized liquid.

Figure 1:
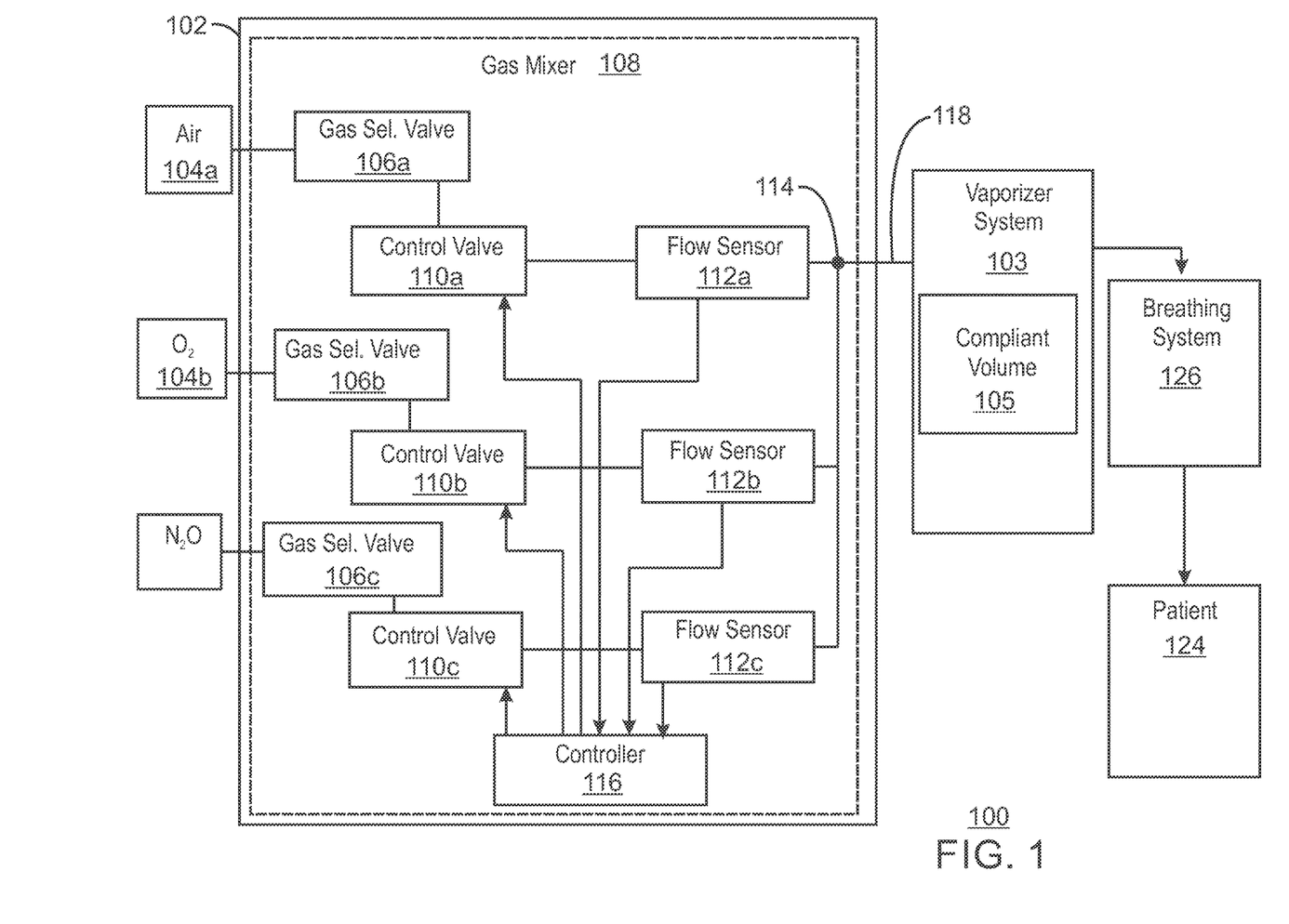
FIG. 1 is a schematic diagram illustrating a vaporizer system used in an anesthesia delivery environment in accordance with an embodiment.

In FIG. 1, an anesthesia system 100 is schematically depicted in accordance with one embodiment. The anesthesia system 100 includes an anesthesia machine 102, a plurality of gas storage devices 104a, 104b and 104c, and a vaporizer system 103. The vaporizer system 103 includes a compliant volume 105. As discussed in more detail below, the compliant volume 105 pressurizes and depressurizes liquid, such as anesthetic liquid.

The anesthesia machine 102 is shown for illustrative purposes and it should be appreciated that other types of anesthesia machines may alternately be implemented. In a typical hospital environment, the gas storage devices 104a, 104b and 104c are centrally located storage tanks configured to supply medical gas to multiple anesthesia machines and multiple hospital rooms. The storage tanks are generally pressurized to facilitate the transfer of the medical gas to the anesthesia machine 102.

The gas storage devices 104a, 104b and 104c will hereinafter be described as including an air tank 104a, oxygen ($O_2$) tank 104b, and a nitrous oxide ($N_2O$) tank 104c, respectively; however it should be appreciated that other storage devices and other types of gas may alternatively be implemented. The gas storage tanks 104a, 104b and 104c are each connected to one of the gas selector valves 106a, 106b, and 106c, respectively, of a gas mixer 108. The gas selector valves 106a, 106b and 106c may be implemented to shut off the flow of medical gas from the storage tanks 104a, 104b and 104c when the anesthesia machine 102 is not operational. When one of the gas selector valves 106a, 106b and 106c is opened, gas from a respective storage tank 104a, 104b and 104c is transferred under pressure to the anesthesia machine 102.

The anesthesia machine 102 includes the gas mixer 108 adapted to receive medical gas from the storage tanks 104a, 104b and 104c. The gas mixer 108 includes a plurality of control valves 110a, 110b and 110c that are respectively connected to one of the gas selector valves 106a, 106b and 106c. The gas mixer 108 also includes a plurality of flow sensors 112a, 112b and 112c that are each disposed downstream from a respective control valve 110a, 110b, and 110c. After passing through one of the control valves 110a, 110b and 110c, and passing by one of the flow sensors 112a, 112b and 112c, the individual gasses (i.e., air, $O_2$ and $N_2O$) are combined to form a carrier gas at a carrier gas outlet 114.

The control valves 110a, 110b, and 110c and the flow sensors 112a, 112b, and 112c are each connected to a controller 116. The controller 116 is configured to operate the control valves 110a, 110b and 110c in a response to gas flow rate feedback from the flow sensors 112a, 112b and 112c. Accordingly, the controller 116 can be implemented to maintain a selectable flow rate for each gas (i.e., air, $O_2$ and $N_2O$) such that the carrier gas at the carrier gas outlet 114 comprises a selectable ratio of air, $O_2$ and $N_2O$.

The carrier gas flows to a pneumatic circuit 118. The vaporizer system 103 introduces anesthetic vapor into the pneumatic circuit 118. Gas within the pneumatic circuit 118 disposed upstream relative to the vaporizer system 103 comprises exclusively carrier gas. Gas within the pneumatic circuit 118 disposed downstream relative to the vaporizer system 103 comprises a mixture of carrier gas and anesthetic vapor and is therefore referred to as mixed gas. The mixed gas is delivered to a patient 124 through a breathing system 126. Although the vaporizer system 103 is schematically depicted as being a separate component of the anesthesia system 100, it should be appreciated that it may alternatively be incorporated into the design of the anesthesia machine 102.

The block diagram of FIG. 1 is not intended to indicate that the anesthesia system 100 is to include all of the components shown in FIG. 1 in every case. Moreover, any number of additional or alternative components not shown in FIG. 1 may be included in the anesthesia system 100, depending on the details of the specific implementation.

Figure 2:
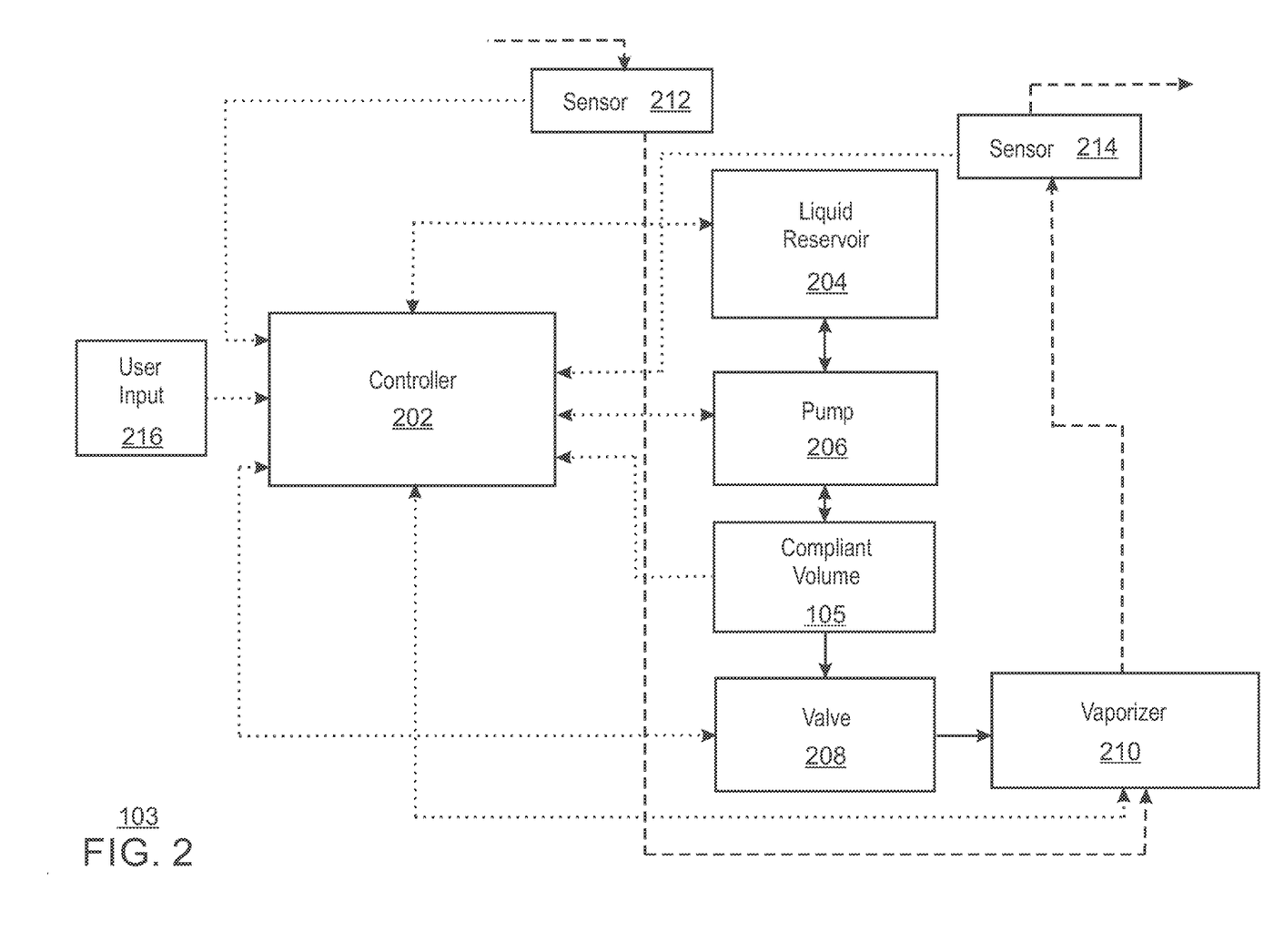
FIG. 2 is a schematic diagram illustrating a vaporizer system in accordance with an embodiment.

FIG. 2 is a schematic diagram illustrating a vaporizer system in accordance with an embodiment. The vaporizer system 103, including the compliant volume 105, is schematically shown in FIG. 2. The vaporizer system 103 may comprise a controller 202, a liquid reservoir 204, a pump 206, a valve 208, a vaporizer 210, a carrier gas sensor 212 and/or a mixed gas sensor 214. In FIG. 2, dotted lines may represent communications between components, dashed lines may represent gas flows between components, and solid lines may represent liquid flows between components.

The controller 202 may be operatively connected to and adapted to receive input signals from a user input 216, the liquid reservoir 204, the pump 206, the valve 208, the vaporizer 210, the carrier gas sensor 212, and the mixed gas sensor 214. The user input 216 may comprise any device adapted to facilitate the transfer of information such as, for example, a keyboard, mouse, touchscreen, dial, trackball, voice recognition device, etc. According to one embodiment, the controller 202 may comprise a computer.

The liquid reservoir 204 is adapted to retain an anesthetic liquid. According to one embodiment the anesthetic liquid may comprise desflurane; however other anesthetics may alternatively be implemented. Those skilled in the art will appreciate that desflurane has a boiling point of 23.5 degrees Celsius at 1 atmosphere pressure such that it can vaporize at or near room temperature. It may therefore be desirable to implement a thermal regulation system and/or pressure regulation system to maintain the anesthetic in its liquid phase until provided to the vaporizer 210. Operating conditions such as temperature, pressure, liquid levels at various components such as the liquid reservoir 204, the pump 206, the compliant volume 105, the valve 208, and/or the vaporizer 210, can be sensed and communicated to the controller 202.

The pump 206 is configured to draw anesthetic liquid from and return anesthetic liquid to the liquid reservoir 204. The pump 206 may comprise a variety of different types of pump such as, for example, a solenoid driven microfluidic pump or a piezoelectric microfluidic pump. In some embodiments, the pump 206 may be a peristaltic pump. As discussed in more detail below, a peristaltic pump may significantly prevent liquid from flowing in either direction when the pump is not active. Therefore, in some scenarios, the vaporizer system 103 may not need a safety shutoff mechanism in addition to the pump 206.

The pump 206 may have a variable frequency that is adjustable within a predefined range to regulate volumetric exchange of anesthetic liquid with the compliant volume 105. Those skilled in the art will appreciate that the frequency of the pump 206 is a measure of the pump's operational speed which may be measured in oscillatory cycles per second. The pump 206 may have a variable duty cycle that is adjustable within a predefined range to regulate volumetric exchange of anesthetic liquid with the compliant volume 105. Those skilled in the art will appreciate that the duty cycle of the pump 206 is a measure of the pump's active time during a larger period of time which may be measured in percent. The pump 206 may have a variable drive level that is adjustable within a predefined range to regulate volumetric exchange of anesthetic liquid with the compliant volume 105. Those skilled in the art will appreciate that the drive level of the pump 206 is a measure of the pump's excitation amplitude which may be measured in volts or amps. The pump 206 may also have a variable stroke length that is adjustable within a predefined range to regulate volumetric exchange of anesthetic liquid with the compliant volume 105. Those skilled in the art will appreciate that the stroke length of the pump 206 is a measure of the mechanical deflection of the pump's operating mechanism (e.g., a diaphragm or piston). The pump 206 may have a forward and a reverse mode of operation to regulate the direction of volumetric exchange of anesthetic liquid with the compliant volume 105. In addition, unidirectional valves (not shown) can be incorporated to pump 206 along the liquid flow passages to direct anesthetic liquid towards the patient only, and to prevent retrograde flow toward the liquid reservoir 204.

The compliant volume 105 may be formed of a resilient and/or elastic material. The compliant volume 105 is capable of cyclically accepting and releasing liquid. As discussed in more detail below, the compliant volume 105 exhibits increasing counter force when expanding, producing increasing liquid pressure as volume is added. Conversely, the compliant volume 105 exhibits decreasing counter force when contracting, producing decreasing liquid pressure as volume is removed. In some scenarios, the expansion or contraction and resulting change of liquid pressure in the compliant volume 105 may be a result of one or more factors of the pump 206. The factors include frequency of the pump cycle, a duty cycle, a drive level, a stroke length of the pump, mode of operating, or any combination of the above.

The valve 208 is selectively operable in an open position or mode in which anesthetic liquid is transferable from the compliant volume 105 to the vaporizer 210. The valve 208 is also selectively operable in a closed position or mode in which anesthetic liquid is precluded from being transferred from the compliant volume to the vaporizer 210. The controller 202 may be implemented to select the operation mode of the valve 208. As an example, the controller 202 may regulate operation of the valve 208 such that anesthetic liquid is transmitted to the vaporizer 210 for delivery to a patient, such as the patient 124 of FIG. 1, in response to a command from the user input 216.

The vaporizer 210 is adapted to convert anesthetic liquid from the valve 208 into anesthetic vapor. The vaporizer 210 may comprise a heat source (not shown) adapted to raise the temperature of the anesthetic liquid and thereby facilitate its conversion to anesthetic vapor. The heat source may, for example, comprise a heated resistive wire, a cartridge heater, a peltier device, a sintered heater, or a passive heating system such as a system comprising heat pipes. Anesthetic vapor from the vaporizer 210 is delivered to the inlet 122 and is then mixed with the carrier gas to form mixed gas. In an alternative embodiment, the carrier gas may be fed directly to the vaporizer 210 to facilitate the vaporization of the anesthetic liquid, and improve the efficiency to mix and transport the anesthetic vapor to form the mixed gas.

The carrier gas sensor 212 and the mixed gas sensor 214 may comprise a known device adapted to measure characteristic features of a fluid. For purposes of this disclosure the term fluid should be defined to include any amorphous substance that continually deforms under an applied shear stress and may therefore include both liquids and gases.

According to one embodiment, the carrier gas sensor 212 is adapted to measure fluid flow rate, and the mixed gas sensor 214 is configured to measure anesthetic vapor concentrations. In another embodiment, both the carrier gas sensor 212 and the mixed gas sensor 214 are configured to measure fluid flow rate, and the comparison of the fluid flow rates provides the measured concentration output of the vaporizer 210, and the amount of anesthetic liquid to be delivered by the pump 206 to achieve the concentration output of the anesthetic vaporizer 210. In yet another embodiment, the anesthetic vapor concentration can be measured directly by sensor 214 configured to detect the concentration of the anesthetic vapor. Known technologies that measure vapor concentrations of anesthetic liquid include but are not limited to infrared, ultrasound, mass spectroscopy, and laser refractometry technologies. Anesthetic vapor concentration can also be measured based on feedback from sensors 212 and 214 respectively configured to assess any physical property (e.g., gas density) of the carrier gas and the mixed gas. A feedback control system incorporating the measured anesthetic vapor concentrations and the user input 216 concentrations can be configured to adjust the operation of pump 206 to achieve the user set vaporizer output concentration, and/or to adjust operation of the pump 206.

Having described exemplary components of the vaporizer system 103, the operation of the vaporizer system 103 will now be described in accordance with an embodiment. The controller 202 may be adapted to receive a target dosage or concentration of anesthetic from the user input 216. Upon receipt of the user requested target concentration, the controller 202 may direct the pump 206 to draw anesthetic liquid from the liquid reservoir 204. The controller 202 may then regulate the pump 206, by way of the pump factors discussed above, to deliver the anesthetic liquid flow rate to the compliant volume 105 in a manner adapted to achieve a given liquid pressure based on the user requested target dosage or concentration of anesthetic. The pressurized anesthetic liquid may then be provided to the valve 208.

In embodiments, the input pressure to the valve 208 may be varied by the compliant volume 105, thereby expanding the flow range of the valve 208. Since valves having a larger liquid flow range may be more expensive than valves with smaller liquid flow ranges, the cost of manufacturing the vaporizer system 103 may be reduced through the use of the compliant volume 105 coupled to the valve 208. Further, because pressurization occurs at the compliant volume 105, the liquid reservoir 204 may be unpressurized. Unpressurized liquid reservoirs may be relatively inexpensive when compared to liquid reservoirs that are configured to provide pressurized liquid to the pump 206. In this manner, overall cost of the vaporizer system 103 may be reduced.

The pressurized anesthetic liquid is provided from the valve 208 to the vaporizer 210, and the anesthetic liquid is converted to anesthetic vapor by the vaporizer 210. The anesthetic vapor is then mixed with the carrier gas to form mixed gas. The mixed gas comprising the user selected target concentration of anesthetic vapor may then be delivered to the patient 124 discussed above in regard to FIG. 1.

As discussed above, the controller 202 may be adapted to operate the valve 208 and the pump 206 based on feedback from the carrier gas sensor 212 and/or the mixed gas sensor 214. As an example, the controller 202 may operate valve 208 and pump 206 to adjust the flow delivery and/or pressurization of the anesthetic liquid based on the carrier gas flow rate (as measured by the carrier gas sensor 212) and/or the mixed gas flow rate (as measured by the mixed gas sensor 214). As another example, the controller 202 may operate valve 208 and pump 206 to adjust the flow delivery and/or pressurization of the anesthetic liquid based on the measured concentration of anesthetic vapor in the mixed gas (as measured by the mixed gas sensor 214).

In some scenarios, the controller 202 may receive information related to variables such as a carrier gas flow rate from the sensor 212, user input 216, mixed gas concentration from the sensor 214, and pressure feedback from the compliant volume 105. Based on the information received, the controller 202 may perform operations such as adjusting operation of the pump, adjusting operation of the valve, and the like.

Figure 3:
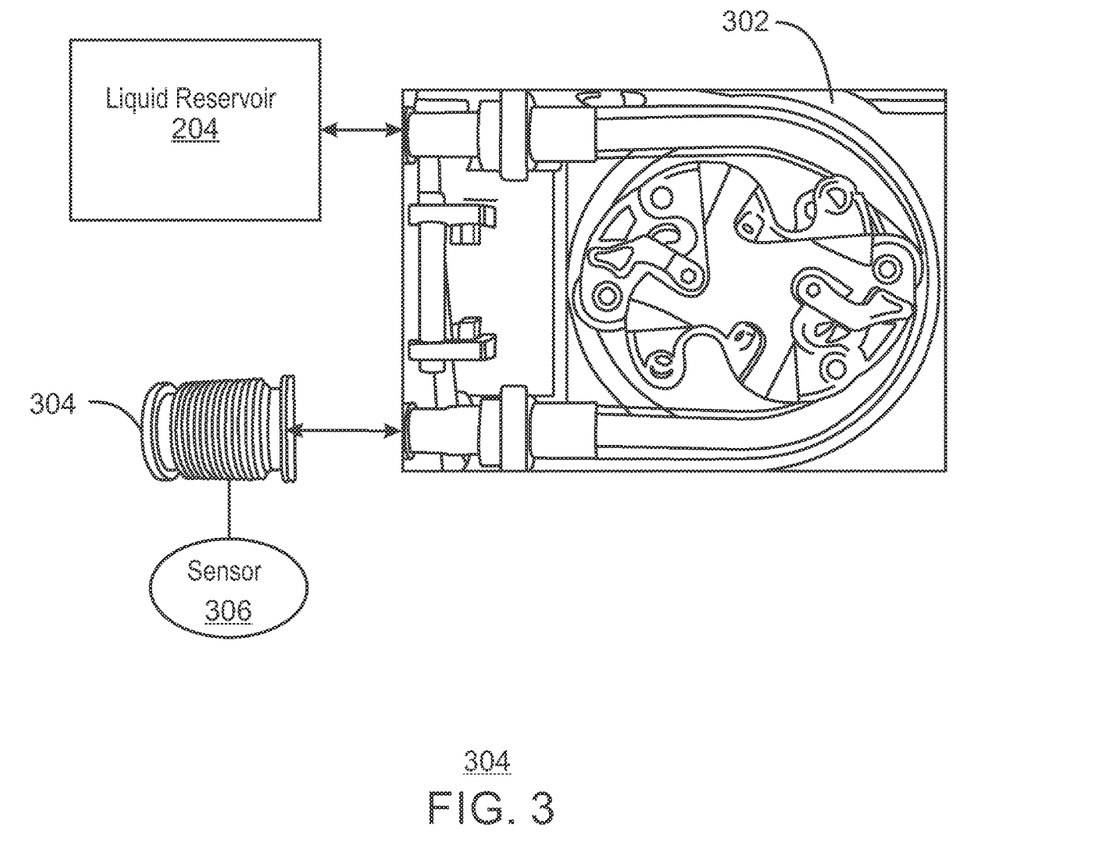
FIG. 3 illustrates a portion of a vaporizer system including a pump and a compliant volume.

FIG. 3 illustrates a portion of a vaporizer system including a pump and a compliant volume. In the example illustrated in FIG. 3, the pump 206 of FIG. 2 is a peristaltic pump, indicated at 302. The compliant volume 105 is a metal bellows, indicated at 304. In this scenario, the peristaltic pump 302 may draw liquid from or return liquid to the liquid reservoir 204, and provide the liquid to or draw liquid from the metal bellows 304. When deactivated, or turned off, the peristaltic pump 302 may significantly prevent liquid from flowing in either direction. Therefore, in some embodiments, an external safety mechanism providing the similar functionality may not be required. As the accumulated liquid volume provided by peristaltic pump 302 to the metal bellows 304 increases, an elastic counter force of the metal bellows 304 may increase, thereby increasing the pressure of the liquid provided to a valve of the vaporizer system, such as the valve 208 in the vaporizer system 103 discussed above in regard to FIG. 2. As the accumulated liquid volume drawn by peristaltic pump 302 from the metal bellows 304 increases, an elastic counter force of the metal bellows 304 may decrease, thereby decreasing the pressure of the liquid provided to a valve of the vaporizer system, such as the valve 208 in the vaporizer system 103 discussed above in regard to FIG. 2. As discussed above in regard to the pump 206 of FIG. 2, a number of factors of operation of the peristaltic pump 302 may affect the pressurization applied to the liquid by the metal bellows 304, such as frequency, duty cycle, drive level, stroke length, forward or reverse operating mode, and the like.

In some embodiments, one or more sensors 306 may be included as a part of, or connected to, the metal bellows 304. For example, the metal bellows 304 may incorporate a pressure sensor, a strain sensor, a displacement sensor, and the like. The sensor 306 incorporated with the metal bellows 304 may provide feedback related to various conditions associated with the metal bellows, and a vaporizer system in general, such as the vaporizer system discussed above in regard to FIG. 1 and FIG. 2.

Figure 4:
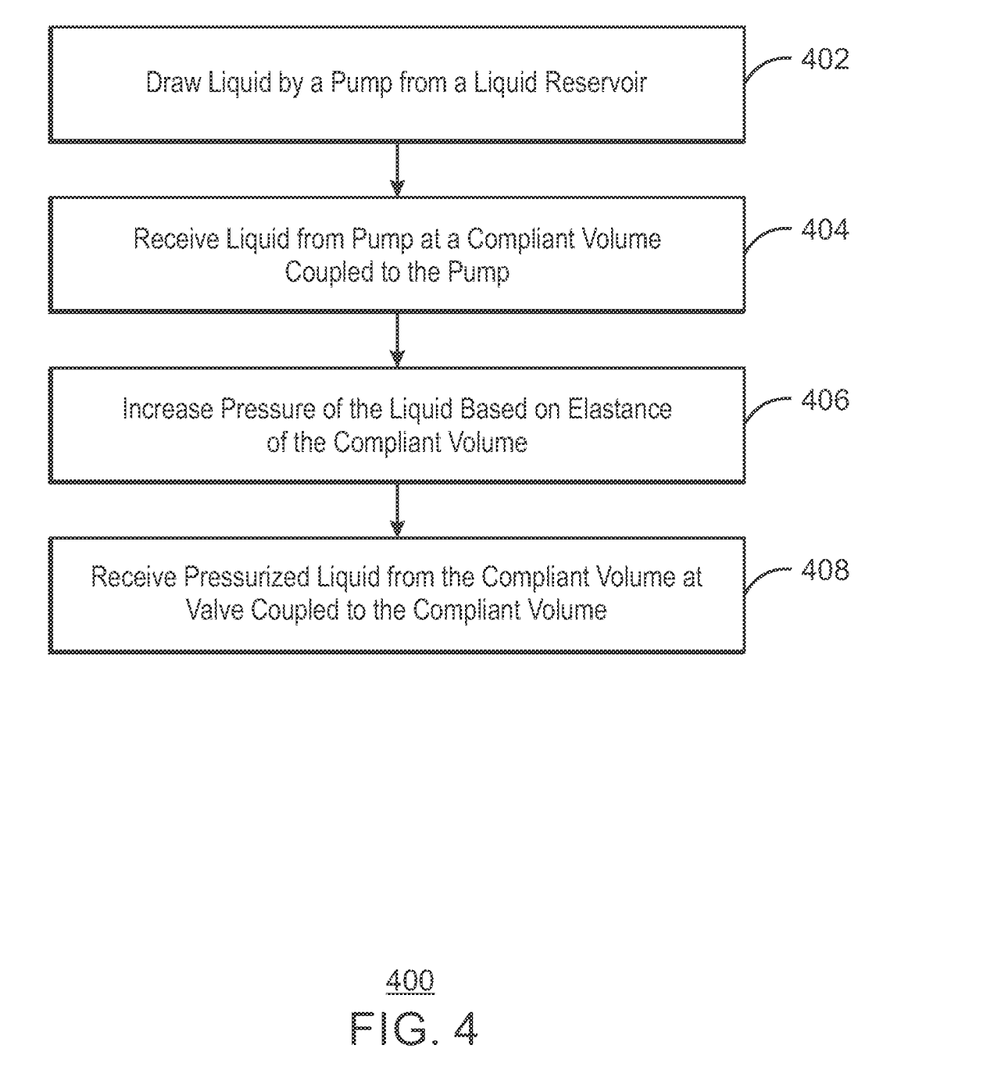
FIG. 4 is a block diagram illustrating a method for pressurizing liquid.

FIG. 4 is a block diagram illustrating a method for pressurizing and depressurizing liquid. At block 402, liquid is drawn by a pump from a liquid reservoir. At block 404, the liquid is received from the pump at a compliant volume. The compliant volume is configured to be resilient and/or elastic, having a counter force to expansion. When the liquid is received at the compliant volume, depending on the volume of liquid received, the pressure of the liquid is increased based on the counter force to expansion of the compliant volume, as indicated at block 406. The pressurized liquid is received at a valve coupled to the compliant volume, as indicated at block 408.

In embodiments, the method 400 includes receiving the pressurized liquid from the valve at a vaporizer coupled to the valve. The specific pressurization of the liquid provided to the vaporizer may be dependent on a dosage and/or a desired concentration of anesthetic vapor to be provided to a patient, as discussed above in regard to FIG. 2.

Receiving the liquid at the compliant volume may include receiving liquid from the pump at an inlet port of the compliant volume, and providing pressurized liquid from an outlet port of the compliant volume to the valve. In other words, in embodiments, the compliant volume is downstream from the pump, rather than an integrated component of the pump.

Further, the method 400 may include depressurization of liquid. For example, liquid that is pressurized in the compliant volume may be depressurized based on a given dosage and/or a desired concentration of anesthetic vapor to be provided to the patient, as discussed above in regard to FIG. 2.

In some embodiments, the pressure range of the valve is smaller than a pressure range of the compliant volume. As discussed above in regard to FIG. 2, the compliant volume may effectively increase the liquid flow range of the vaporizer system 103 without necessarily using a valve that has an increased liquid flow range itself.

While embodiments are described herein with respect to vaporizing systems used in the medical field, the reference to vaporizing systems may be interpreted broadly. Further, those of skill in the art will recognize that the present techniques are applicable to many different architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for pressurizing liquid, comprising:
 a liquid reservoir;
 a pump coupled to the liquid reservoir, the pump to draw liquid from the liquid reservoir;
 a compliant volume coupled to the pump to receive liquid from pump, the compliant volume composed of an elastic material to increase pressure of the liquid as volume of the compliant volume is increased;
 a valve coupled to the compliant volume to receive pressurized liquid from the compliant volume, wherein an input pressure to the valve is varied by the compliant volume; and
 a vaporizer coupled to the valve to receive the liquid from the valve, wherein a flow rate of the liquid is based, in part, on an elastance of the compliant volume.

2. The system of claim 1, wherein the compliant volume is to decrease pressure of the liquid as the volume of the compliant volume is decreased.

3. The system of claim 1, wherein the compliant volume comprises:
 an inlet port to receive liquid from the pump; and
 an outlet port to provide pressurized liquid to the valve.

4. The system of claim 1, wherein the compliant volume comprises a resiliently deformable bellows.

5. The system of claim 1, wherein the pressure of the pressurized liquid depends in part on factors of the pump, the factors comprising:
 frequency of the pump cycle;
 a duty cycle;
 a drive level;
 a stroke length of the pump;
 a mode of operation of the pump; or
 any combination of the above.

6. The system of claim 1, wherein the pump is configured to provide liquid to, and draw liquid from, the compliant volume.

7. A method for pressurizing liquid, comprising:
drawing liquid by a pump from a liquid reservoir;
receiving liquid from pump at a compliant volume coupled to the pump, wherein the compliant volume is composed of an elastic material to increase pressure of the liquid as volume of the compliant volume is increased;
receiving pressurized liquid from the compliant volume at a valve coupled to the compliant volume, wherein an input pressure to the valve is varied by the compliant volume; and
receiving the liquid from the valve at a vaporizer coupled to the valve, wherein a flow rate of the liquid is based, in part, on an elastance of the compliant volume.

8. The method of claim 7, wherein receiving liquid at the compliant volume comprises:
receiving liquid from the pump at an inlet port of the compliant volume; and
providing pressurized liquid from an outlet port of the compliant volume to the valve.

9. The method of claim 7, wherein the pressure of the pressurized liquid depends in part on factors of the pump, the factors comprising:
frequency of the pump cycle;
a duty cycle;
a drive level;
stroke length of the pump;
a mode of operation of the pump; or
any combination of the above.

10. An anesthetic vaporizer apparatus, comprising:
a liquid reservoir;
a pump coupled to the liquid reservoir, the pump to draw liquid from the liquid reservoir;
a compliant volume coupled to the pump to receive liquid from the pump, the compliant volume composed of a resilient material to increase pressure of the liquid;
a valve coupled to the compliant volume to receive pressurized liquid from the compliant volume; and
a vaporizer coupled to the valve to receive the liquid from the valve, wherein a flow rate of the liquid is based, in part, on an elastance of the compliant volume.

11. The anesthetic vaporizer apparatus of claim 10, wherein the pump comprises a shut-off position to substantially prevent liquid from being drawn from the liquid reservoir, or sliding back to the liquid reservoir.

12. The anesthetic vaporizer apparatus of claim 10, wherein an input pressure to the valve is varied by the compliant volume.

13. The anesthetic vaporizer apparatus of claim 10, wherein the compliant volume comprises a resiliently deformable bellows.

14. The anesthetic vaporizer apparatus of claim 10, wherein the pressure of the pressurized liquid depends in part on factors of the pump, the factors comprising:
frequency of the pump cycle;
a duty cycle;
a drive level;
stroke length of the pump;
a mode of operation of the pump; or
any combination of the above.

15. The anesthetic vaporizer apparatus of claim 10, wherein the pump is configured to provide liquid to, and draw liquid from, the compliant volume.

* * * * *